(12) United States Patent
Nitzan et al.

(10) Patent No.: US 7,340,310 B2
(45) Date of Patent: Mar. 4, 2008

(54) MULTI-LAYERED ELECTRODES AND USES THEREOF

(75) Inventors: Zvi Nitzan, Zofit (IL); Shalom Luski, Rechovet (IL); Mordechay Moshkovich, Ra'anana (IL)

(73) Assignee: Power Paper, Ltd., Petah Tikvah (IL)

( * ) Notice: Subject to any disclaimer, the term of this patent is extended or adjusted under 35 U.S.C. 154(b) by 263 days.

(21) Appl. No.: 11/167,601

(22) Filed: Jun. 28, 2005

(65) Prior Publication Data
US 2005/0284752 A1  Dec. 29, 2005

Related U.S. Application Data

(60) Provisional application No. 60/582,803, filed on Jun. 28, 2004.

(51) Int. Cl.
*A61N 1/04* (2006.01)

(52) U.S. Cl. .................................. 607/129; 607/152

(58) Field of Classification Search ............... 607/129, 607/152
See application file for complete search history.

(56) References Cited

U.S. PATENT DOCUMENTS

| | | | | |
|---|---|---|---|---|
| 4,066,078 A | * | 1/1978 | Berg | ............................ 600/391 |
| 4,934,383 A | | 6/1990 | Glumac et al. | |
| 5,312,326 A | | 5/1994 | Myers et al. | |
| 5,685,837 A | * | 11/1997 | Horstmann | .................... 604/20 |
| 6,263,226 B1 | * | 7/2001 | Axelgaard et al. | ........... 600/391 |
| 2002/0055704 A1 | | 5/2002 | Scott et al. | |
| 2003/0028170 A1 | | 2/2003 | Anderson et al. | |
| 2003/0104271 A1 | | 6/2003 | Maruta et al. | |
| 2003/0205078 A1 | | 11/2003 | Hasei et al. | |
| 2004/0096731 A1 | | 5/2004 | Hama et al. | |

FOREIGN PATENT DOCUMENTS

| | | |
|---|---|---|
| EP | 1548868 A | 6/2005 |
| WO | 2004032274 A1 | 4/2004 |
| WO | 2005004979 A1 | 1/2005 |
| WO | 2005004980 A1 | 1/2005 |

OTHER PUBLICATIONS

International Search Report, European Patent Office, Sep. 16, 2005, Rijswijk, NL.

* cited by examiner

*Primary Examiner*—Carl Layno
*Assistant Examiner*—Brian T. Gedeon
(74) *Attorney, Agent, or Firm*—Kenyon & Kenyon LLP

(57) ABSTRACT

The present invention is of an electrode comprising an electrode substrate, wherein the electrode substrate has an electrode side and a back side; a conductive material layer disposed on the back side of the electrode substrate; and an insoluble electroactive material disposed on the electrode side of the electrode substrate. The electrode substrate can be a conductive substrate or a non-conductive substrate. In an embodiment wherein the substrate is a non-conductive substrate, the electrode can include vias which extend from the electrode substrate backside to the electrode side of the substrate. In some embodiments, the electroactive material is zinc and the conductive material is silver. The present invention provides an electrode with improved current distribution and high capacity, which can provide higher current and/or higher voltage. In addition, the present invention provides a dermal patch, which includes a higher powered, high capacity electrode with uniform current distribution. Still further the present invention provides methods of making the electrode and of attaching the electrode to a power source.

14 Claims, 5 Drawing Sheets

MULTI-LAYERED ELECTRODES AND USES THEREOF

This application claims priority to U.S. Provisional Application Ser. No. 60/582,803, filed Jun. 28, 2004 and incorporated by reference herein in its entirety.

FIELD OF THE INVENTION

The present invention relates to electrodes and uses thereof.

BACKGROUND OF THE INVENTION

Numerous types of electrodes are typically used in a variety of diverse applications. Electrode structure and characteristics are usually dependent on the application of the electrode.

One type of electrode of the background art comprises a non-conductive substrate layer, such as a polyester layer with an insoluble electroactive material coated on at least one side. Electrical contacts must be placed on the same side as the insoluble electroactive material, resulting in non-symmetrical current distribution. However, non-symmetrical current distribution is not desirable in for example transdermal delivery systems. In such systems, if the current is not uniform, drug delivery may not be uniform and a concentrated current at one electrode point can cause burning and/or irritation of the skin.

In applications of transdermal delivery systems, wherein a high delivery rate is desired, it is also advantageous to have an active electrode with a high capacity. Further, in a transdermal delivery system, wherein released electroactive material ions are to be delivered and used for treatment, electrode high capacity is preferred.

An accepted method of producing thin and flexible electrodes is using conductive vinyl web. However, vinyl web has relatively high sheet resistance and when an active electrode is not regular in shape and size, there is significant differences in the resistance along the length of the electrode, resulting in uneven current distribution.

There is thus a recognized need for, and it would be highly advantageous to have, an electrode, which can provide, uniform and high current density (current distribution) and which has properties of low sheet resistance and high capacity. Still further it would be advantageous to have a method of producing an electrode with low sheet resistance, high capacity and uniform current distribution.

BRIEF DESCRIPTION OF THE DRAWINGS

With reference now to the drawings in detail, it is stressed that the particulars shown, are by way of example and for the purposes of illustrative discussion of embodiments of the present invention only, and are presented for providing what is believed to be the most useful and readily understood description of the principles and conceptual aspects of the invention. In this regard, no attempt is made to show structural details in more detail than is necessary for a fundamental understanding of the invention, the description taken with the drawings making apparent to those skilled in the art how the several forms of the invention may be embodied in practice.

In the drawings.

DETAILED DESCRIPTION OF THE PREFERRED EMBODIMENTS

Figure 1:
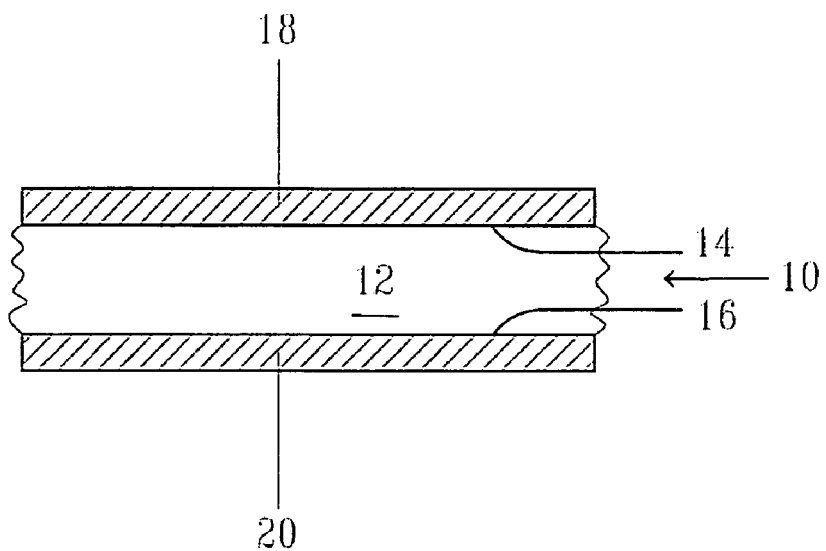
FIG. 1 shows a schematic view of an electrode according to an embodiment of the present invention.

The present invention provides an electrode with improved current distribution, low sheet resistance and high capacity and methods of production thereof and attachment to a power source. In some embodiments, the electrode is a higher powered electrode, which provides higher current (compared to inert electrodes, such as graphite electrodes of the art used in the same electrode system).

The terms 'higher power' and 'higher current' as used herein are relative terms and refer to higher power or higher current, which result from the electrode of the present invention when used in an electrode system compared to the power and current resulting from an inert electrode of the art used in the same electrode system. The term 'higher voltage' as used herein is a relative term and refers to the electrode of the present invention facilitating supporting a higher voltage in an electrode system compared to the voltage supported by an inert electrode in the same system.

Embodiments of the present invention also provide uses of higher power, higher current, uniform current distribution and high capacity electrodes which include, but are not limited to uses in for example dermal and transdermal delivery devices.

Embodiments of the electrodes of the present invention may comprise an electrode substrate with two sides, an electrode side and a backside. The term 'electrode side' as used herein refers to the side of the substrate on which an insoluble electroactive material is disposed and which facilitates electrochemical reaction. The term includes an electrode side, which is not ionically connected to the backside. The term 'backside' as used herein refers to a side of the substrate that is opposite to the electrode side. The term includes a backside of the substrate, which is not ionically connected to the electrode side. Further, the term can include a substrate side on which a conductive material is disposed, wherein the conductive material is not configured as an electroactive pole material. An electrode substrate backside may be coated with at least one conductor. An electrode substrate electrode side may be coated with at least one insoluble electroactive substance. In some embodiments, the electrode substrate is a conductive substrate.

Embodiments of the present invention may include electrodes, which may comprise a non-conductive electrode substrate with two sides, an electrode side and a backside and a plurality of vias, which extend from the backside to the electrode side of the electrode substrate.

Embodiments of the present invention may provide a higher power zinc electrode, which may comprise an electrode substrate with two sides, wherein a backside may be coated with a conductor and an electrode side may be coated with zinc.

Embodiments of the present invention may electrochemically generate metal ions. In some embodiments the metal ions can be used for therapeutic and/or cosmetic treatment of a biodisorder.

Embodiments of the present invention may include a device, which may comprise first and second electrodes and a power source, wherein at least one of first and second electrodes have a structure as described above.

Embodiments of the methods of use of the present invention may also comprise providing a device for treatment of a body area disorder, wherein the device comprises an electricity generating device, which may include, but is not limited to an electro-transportation device, iontophoresis device, a bio-membrane patch, a dermal patch, a galvanic stimulation device, an electrokinetic device, an electroporation device, an ultrasound device, a microneedle, a TENS device and a combination thereof, and wherein the device includes at least one electrode of the present invention as described herein. The device can be a flexible, wearable patch conformable to the contour of a body area surface. The method further includes contacting the body area with the device for a time period wherein the device promotes uniform, high rate active ingredient agent penetration of the body area surface and underlying tissues, penetrating of the active ingredient into and/or onto the body area to treat the body area disorder, and removing the device from the body area.

Figure 5:
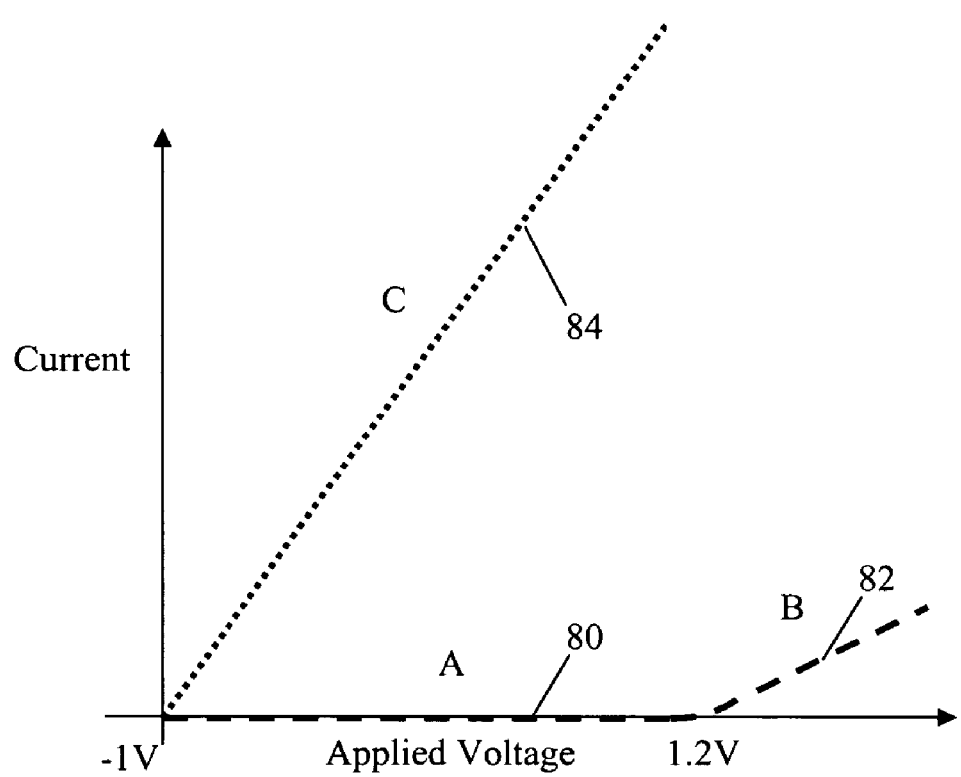
FIG. 5 shows a graphical representation of the 'knee effect'.

An inherent problem associated with the use of prior art inert graphite anode electrodes is the 'knee phenomenon', which results in substantial current flow only if the applied potential, is above about 1.2V. Due to the 'knee phenomenon' the use of a single 1.5V battery and an inert graphite electrode results in very low current and uneven current distribution. In an example wherein a graphite electrode is connected to a 1.5V battery (that is about 1.4V closed circuit voltage (CCV)), the effective working voltage is only about 0.2V. When such a graphite electrode is connected to two batteries (2.8V closed circuit voltage), the effective working voltage is only about 1.6V. A solution to achieve a higher working voltage and to improve the efficiency of the inert electrode, may be to coat or replace the graphite electrode with an electroactive material such as zinc. In such a way the electrode is effectively converted to an active electrode, that lowers or eliminates the 'knee effect'. As a result of, for example, the zinc coating, and the use of silver/silver chloride counter electrode, it is possible to achieve with only one battery, a working voltage of greater than about 2V and respective higher current. FIG. 5 shows a graphical representation of the 'knee effect' as known in the art. FIG. 5 is an I-V curve of current response as a function of voltage change of electrochemical systems, which include an anode (graphite/zinc) and cathode (Ag/AgCl) in an aqueous solution. The segment 80 of the lower trace marked A represents the electrochemical behavior of a system with a graphite electrode, wherein at a voltage of lower than about 1.2V there is no substantial current flow. The segment 82 of the lower trace marked B shows the electrochemical behavior of a system with a graphite electrode, wherein at a voltage of above about 1.2V, there is substantial current flow. The upper trace 84 marked C represents a generalized electrochemical behavior of a system with a zinc electrode. It is noted that there is much higher current than the graphite electrode system (B) and substantial current flow below 1.2V.

However, an additional problem of thin and flexible electrodes is the uneven current distribution. An accepted industrial method of producing thin and flexible electrodes is using a conductive vinyl web substrate. The sheet resistance of such material is about 100-300 ohms/square. When the vinyl web is coated with zinc and the active electrode is very large and in a non-regular shape, the resulting current distribution is not generally symmetrical; it may be high in the area of the connection to, for example, a body area, and low at the ends of the electrode.

In order to overcome these problems, the present invention provides an electrode coated with a thin layer of conductive material, such as but not limited to silver, of from about 1 to about 10 microns. Optionally, thicker or thinner layers of conductive material can be used. The conductive material coating, such as silver coating facilitates lowering the sheet resistance of the electrode from about 100-300 ohms/square to about 1-3 ohms/square. As a result, the current output is higher, the electrode capacity increases and the current is generally symmetrical. The resulting electrode provided by the present invention is significantly more efficient.

Before explaining at least one embodiment of the invention in detail, it is to be understood that the invention is not limited in this application to the details of construction and the arrangement of the components set forth in the following description or illustrated in the drawings. The invention is applicable to other embodiments of being practiced or carried out in various ways. Also, it is to be understood that the phraseology and terminology employed herein is for the purpose of description and should not be regarded as limiting.

The principles and operation of electrodes and devices according to the present invention may be better understood with reference to the figures. The figures show several embodiments of the present invention and are not limiting.

In one embodiment of the electrode of the present invention as shown in FIG. 1, electrode 10 includes an electrode substrate 12 with at least two sides, one side which is preferably the electrode side 14 and a second side, which is preferably a backside 16. In some embodiments, electrode substrate 12 is made of any suitable conductive material. A non-limiting example of a conductive material is vinyl web. A conductive electrode substrate 12 can readily facilitate current flow from the two sides of the electrode. As such, in the case where electrical contact is made from the backside 16 of the electrode substrate, current which is produced during electrochemical processes from the electrode side 14 of electrode substrate 12 can be collected.

In some embodiments, the electrode side 14 of electrode substrate 12 can be coated with an insoluble electroactive material 18. Electroactive material 18 can be applied onto electrode side 14 of electrode substrate 12 using any suitable technique. Electroactive material 18 can be in any suitable form, including but not limited to an ink, powder or foil. In some embodiments wherein a printing technique is employed, an ink containing insoluble electroactive material 18 is printed onto electrode side 14 of electrode substrate 12 using a suitable printing technique, which includes but is not limited to silk print, offset print, jet printing, laminations, material evaporations and powder dispersion and spray printing. Examples of suitable insoluble electroactive materials 18 include, but are not limited to zinc, copper, magnesium, silver, silver/silver chloride and iron. In some embodiments, insoluble electroactive material 18 is zinc. In some embodiments, insoluble electroactive material 18 can be a combination or mixture of insoluble electroactive materials, such as for example an alloy.

The purity of the electroactive material 18 or ink depends on the function of electrode 10. In a case wherein electrode 10 is for use in a battery, toxic anti corrosive additives can be added to the material, which can be in the form of an ink to prevent corrosion of electroactive material 18, such as for example zinc alloy. However, in an example, wherein electrode 10 is for use in a dermal/transdermal delivery system or any electrotransport delivery system, the electroactive material 18 is preferably a relatively pure material 18, without toxic anti-corrosive additives. These additives are avoided, in order to prevent poisoning from toxic ions, such as for example indium ions. In an embodiment, wherein the electroactive material 18 is contained in an ink, the amount of insoluble electroactive material used in the ink can be arbitrary, but preferably is determined according to desired capacity and is in the range of from about 1% to about 95%. In one non-limiting example the ink includes about 50% (% W) insoluble electroactive material 18 and about 50% (% W) additives. The more electroactive material 18 included in the ink, the higher the capacity. In some embodiments, the electroactive ink contains additives, such as, but not limited to solvent, binder and conductive particles. The ink can be applied in any way, such as printed onto the electrode substrate to result in any desired electrode thickness. The thicker the electroactive material layer, the higher the load, which is proportional to a higher capacity. The thickness of the electroactive material dry layer can be from about 10 microns to about 100 microns. In some embodiments, electroactive dry layer thickness is up to about 50 microns, however thicker or thinner layers can be achieved.

In some embodiments, the backside 16 of electrode substrate 12 is coated with a conductive material 20. Any suitable conductive substance 20 can be used including, but not limited to silver, silver/silver chloride, gold and platinum and carbon (graphite). In some embodiments, the conductive substance 20 is silver. Any suitable form of conductive material can be use, such as, but not limited to an ink containing conductive material or a conductive adhesive containing conductive material. In some embodiments, conductive substance 20 is a less reactive substance than insoluble electroactive material 18. Conductive material 20 can be coated onto the electrode substrate using any suitable technique. In some embodiments, conductive material 20 can be printed onto the back side 16 of the electrode substrate using a suitable printing technique. Optionally, the thickness of the layer of conductive material can be from about 1 to about 50 microns. In some embodiments, the thickness of the layer of conductive material can be from about 1 to about 10 microns. An electrode 10, which includes a conductive material 20 on the backside of the substrate readily conducts current and facilitates an electrode with homogeneous, uniform current distribution. Because conductivity of the electrode is increased, higher currents can be supplied, the sheet resistance is lowered and the capacity can be higher. In a non-limiting example, wherein conductive material 20 is silver, the silver will not substantially react until the more reactive insoluble electroactive material 18 forming the electrode side 14 of electrode substrate 12, for example zinc, is depleted. Optionally, electrode 10 can be any suitable electrode, such as a cathode or an anode, an active electrode, main electrode or a counter electrode. In some embodiments, electrode 10 is an anode.

Figure 2:
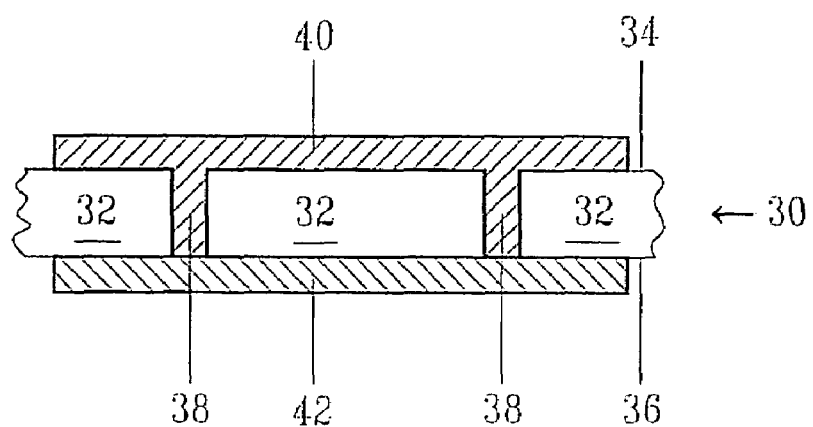
FIG. 2 shows a schematic view of an electrode according to an alternate embodiment of the invention.

In an alternative embodiment as shown in FIG. 2, electrode 30 includes an electrode substrate 32 with at least two sides, one side which is preferably the electrode side 34 and a second side, which is preferably a backside 36. In some embodiments, electrode substrate 32 is made of any suitable non-conductive material. In some embodiments, non-conductive material is polyester. In some embodiments, non-conductive electrode substrate 32 includes vias (holes) 38, which are configured to connect between electrode side 34 of electrode substrate 32 and backside 36 of electrode substrate 32. Vias (holes) 38 can provide a means for current conduction between the two sides of electrode substrate 32. In some embodiments, electrode side 34 can be coated with an insoluble electroactive material 40. In some embodiments, backside 36 can be coated with a conductive material 42. In some embodiments vias 38 can be coated with conductive material 42 or electroactive pole material 40 or a combination thereof. In FIG. 2, vias are coated with electroactive material 40.

The properties and description of insoluble electroactive material 40 and conductive material 42 are the same as described for FIG. 1. An electrode 30, which includes a conductive material 42 readily conducts current through the vias and facilitates an electrode with homogeneous, uniform current distribution. Because conductivity of the electrode is increased, higher currents can be supplied, sheet resistance is lowered and capacity can be higher.

Optionally, electrode 30 can be any suitable electrode, such as a cathode or an anode, an active electrode, main electrode or a counter electrode. One of the advantages of the embodiment of the electrode described in FIG. 2 compared to the embodiment described in FIG. 1 is that use of a non-conductive substrate can be less expensive than a conductive substrate and is sometimes more suitable for certain production methods.

The electrodes of the present invention have a wide range of uses, which include, but are not limited to use in batteries, in passive and active, thin and non-thin, flexible and non-flexible dermal/transdermal/electrotransport delivery systems and electrostimulation systems.

In one example wherein the electrode of the present invention is a zinc electrode and the electrode is connected in any suitable way to a battery, the resulting electrode can provide higher current and support higher voltage. In some embodiments the electrode is connected to the battery with a conductive adhesive. Any suitable conductive pressure sensitive adhesives or conductive adhesives can be used.

In an example, wherein the electrode of the present invention is used in an iontophoretic patch or any suitable dermal or transdermal or electrotransport delivery system, higher current can facilitate higher delivery rate and therefore higher efficiency of the delivery system. Higher voltage can also facilitate penetration of skin, by for example facilitating electroporation and therefore is advantageous in a patch or delivery system for better penetration and delivery of a substance into the skin. The electrode of the present invention, which is configured to facilitate homogeneous current distribution enables higher currents to be used without the unwanted problems of skin burning or non-uniform drug delivery.

The electrodes of the present invention can be protected during storage and before use from for example corrosion or reaction with moisture and air by using any technique as known in the art, such as vacuum packaging or storing in an atmosphere of inert gas. Further protective means include, coating the insoluble pole electroactive material with a thin layer of more reactive material, which can be depleted during storage or initially on use. An alternative protective means includes coating with a protective water soluble material.

Figure 3A:
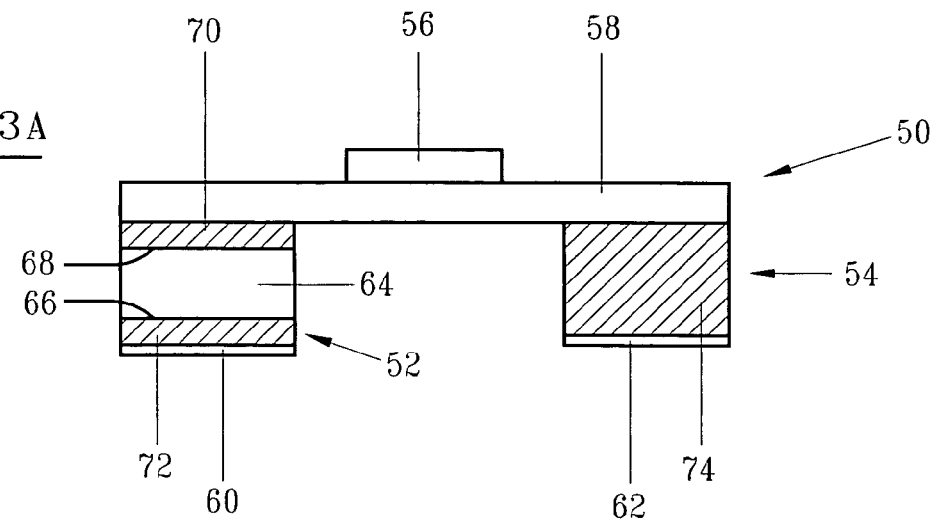
FIG. 3A shows a schematic view of a dermal patch including a higher power electrode according to one embodiment of the invention.

FIG. 3A shows a schematic view of one non-limiting example of an electrotransport device, such as a dermal patch 50 including a higher powered electrode according to one embodiment of the present invention. As can be seen from FIG. 3, patch 50 includes an active electrode 52, a counter electrode 54 and a battery or any other suitable power source 56 disposed on a base layer substrate 58. Optionally, patch 50 may include a plurality of active electrodes 52, a plurality of counter electrodes 54 and a plurality of power sources 56. Patch 50 may also comprise conductive layer/s 60 and 62 to provide an interfacing layer between patch 50 and a body area of a subject. As shown in FIG. 3, electrodes 52, 54, conductive layers 60, 62, and electrochemical cell may be supported on substrate 58. In some embodiments, active electrode 52 is a zinc electrode. Zinc electrode 52 may be disposed in any suitable way on substrate 58 in spaced relation to electrochemical cell 56 and electrode 54 to define a gap between the two electrodes. Conductive layer/s 60 and 62 may optionally be disposed on electrode 52 or 54 or on both electrodes 52 and 54

In some embodiments, patch 50, including patch components, is thin and flexible, to suit the contour of a body area of a subject. In some embodiments, patch 50 is electrically powered. Patch 50 may be any size, color and shape suitable for application to a desired body area. The thickness of patch 50 is preferably up to 10 mm to ensure flexibility, but may be thicker, depending on the application. The thickness of the patch may also be dependent upon the type of material used and the flexibility of that material. Patch 50 is preferably disposable, but may be reusable. Patch 50 is stable to a wide range of temperatures and humidity.

Any power source 56, of any size or shape, which provides an electrical potential of between about 0.2 Volt and about 100 Volt can be used according to the present invention. Yet, in a preferred embodiment, power source 56 is an electrical battery, providing an electrical potential of between about 1.5 Volt and 25 Volt.

In some embodiments, power source 56 is thin and flexible. In some embodiments, power source thickness should not exceed 4 mm and more preferably, power source thickness should be less than 2 mm. In a further preferred embodiment, power source 56 is at least one electrochemical cell. The term 'electrochemical cell' as used herein includes any suitable cell in which chemical energy is converted to electric energy by a spontaneous electron transfer reaction. The term includes cells with non-spontaneous reactions, cells with spontaneous reactions, galvanic cells, electrolytic cells and a combination thereof. In some embodiments, electrochemical cell includes a first layer of insoluble negative pole, a second layer of insoluble positive pole and a third layer of aqueous electrolyte, the third layer being disposed between the first and second layers and including: (a) a deliquescent material for keeping the open cell wet at all times; (b) an electroactive soluble material for obtaining required ionic conductivity; and (c) a water soluble polymer for obtaining a required viscosity for adhering the first and second layers to the third layer. Such a power source is described in U.S. Pat. Nos. 5,652,043, 5,811,204 and 5,897,522, which are incorporated herein by reference in their entireties. Additional details can also be found at www.powerpaper.com. However, the use of any power source consistent with a flexible wearable device, or any power source consistent with a non-flexible wearable device, is within the scope of the invention.

Optionally, power source 56 in patch 50 is a single electrochemical cell. However, power source 56 need not be limited to one cell, but may include a plurality of connected electrochemical cells, a plurality of batteries, and/or electronics configured to increase, control, and change phase of the supplied electric current and wherein the power source is thin and flexible. Electrochemical cell 56 in patch 50 preferably provides electrical potential (voltage) to the desired body area of the subject.

The power source may optionally be located in any suitable position on the patch.

In some embodiments, active electrode 52, which can in some embodiments be a zinc electrode, includes electrode substrate 64 with at least two sides, one side which is preferably the electrode side 66 and a second side, which is preferably an electrode substrate backside 68. In some embodiments, electrode substrate 64 is made of any suitable conductive material. A preferred conductive material is vinyl web. A conductive electrode substrate 64 can readily facilitate current flow from the two sides of the electrode. As such, in the case where electrical contact is made from the backside 68 of the substrate, current which is produced during electrochemical processes from the electrode side 66 of electrode substrate 64 can be collected and used.

In some embodiments, the electrode side 66 of electrode substrate 64 is coated with an insoluble electroactive substance 72, such as, but not limited to zinc. Electroactive substance, such as, but not limited to zinc can be applied onto electrode side 66 of electrode substrate 64 using any suitable technique. In some embodiments, an ink containing zinc is printed onto electrode side 66 of electrode substrate 64 using a suitable printing technique. The ink including the electroactive substance, such as zinc can be a relatively pure ink, without toxic anti-corrosive additives. These additives are avoided, in order to prevent poisoning from toxic ions, such as for example indium ions. The amount of electroactive material used in the ink can be arbitrary, but in some embodiments is determined according to desired capacity. In one non-limiting example the ink includes about 50% (% W) electroactive substance, such as zinc. The more electroactive substance, such as zinc in the ink, the higher the capacity. In some embodiments, the ink including the electroactive substance, such as zinc contains additives, such as, but not limited to solvent, binder and conductive particles. The ink can be any suitable ink, such as, but not limited to a solvent based ink or a UV based ink. The ink can be printed onto the substrate to result in any desired electrode thickness. The thicker the electroactive layer, the higher the load, which is proportional to a higher capacity. A preferred electroactive dry layer thickness is up to about 50 microns, however higher or lower is achievable.

In some embodiments, the backside 68 of electrode substrate 64 is coated with a conductive material 70. Any suitable conductive substance 70 can be used including, but not limited to silver, silver/silver chloride, gold and platinum. In some embodiments, the conductive substance 70 is silver. Conductive material can be coated onto the substrate using any suitable technique. In some embodiments, conductive material is printed onto the backside 68 of the substrate 64 using a suitable printing technique. In some embodiments, conductive material layer is very thin, about a few microns thick. In some embodiments, the thickness of the layer of conductive material is from about 1 to about 10 microns. In some embodiments, the thickness of the layer of conductive material is from about 1 to about 4 microns.

Figure 3B:
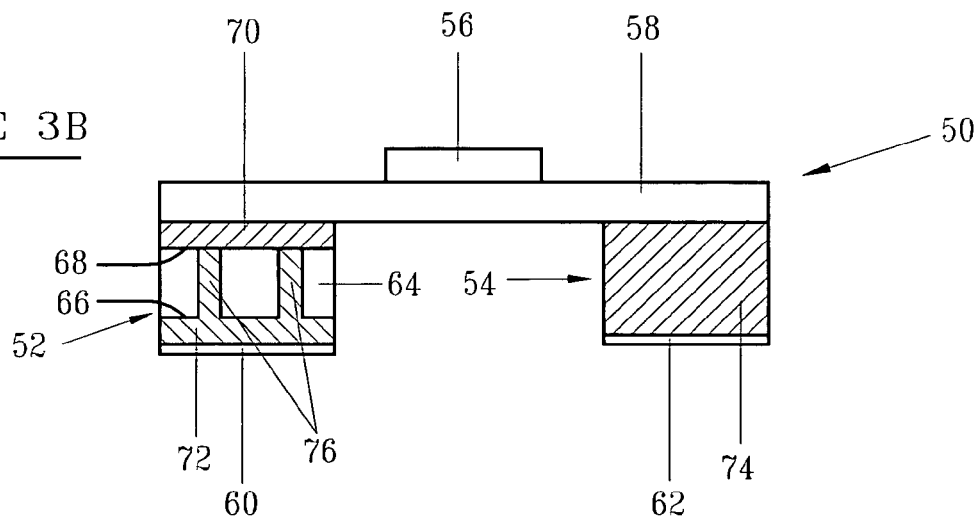
FIG. 3B shows a schematic view of a dermal patch including a higher power electrode according to an alternate embodiment of the invention.

In an alternative embodiment, as shown in FIG. 3B, active electrode 52, such as but not limited to zinc electrode includes a non-conductive electrode substrate with two sides, an electrode side and a backside and a plurality of vias 76, which extend from the backside 68 to the electrode side 66 of the electrode substrate 64 as described in FIG. 2.

Active electrode 52, such as, but not limited to zinc electrode, which includes a relatively non-reactive conductive material readily conducts current and facilitates an electrode with homogeneous, uniform current distribution. Because conductivity of the electrode is increased, higher currents can be supplied.

In some embodiments, electrode 52, such as a zinc electrode is an active electrode and at least one additional electrode 54 is a counter electrode. In some embodiments, counter electrode 54 can be any suitable counter electrode and can include any suitable material 74, such as but not limited to silver/silver chloride. Optionally, both electrodes 52, 54 can be active electrodes. The electrodes 52, 54 may optionally be provided in any suitable form, such as, but not limited to as thin sheets, linked to the power source, or printed onto a substrate in spaced relation to each other to define a gap therebetween. Optionally, the electrode area can be continuous, or formed in any shape or configuration. Optionally, zinc electrode 52 and counter electrode 54 may not have the same shape and/or same area. Optionally, cathode and anode may be in any suitable conformation in relation to each other including but not limited to a coplanar and cofacial arrangement. Optionally, patch can include a plurality of anodes and a plurality of cathodes.

In some embodiments, active electrode 52, such as, but not limited to zinc electrode and counter electrode 54 are connected to battery 56 by any suitable connection means, such as electrical conduction means/media. Examples of connection means include, but are not limited to wiring, conductive ink, printed connection means, soldered connection means, connection means attached by UV, adhesive connection means and a combination thereof. In some embodiments, electrodes are connected to battery using conductive adhesive.

Base layer substrate 58 is optionally any suitable material, which can accommodate the patch components. Suitable materials include, but are not limited to woven material, non-woven material, polymers, conducting material, non-conducting material, paper, cardboard, plastic, synthetic materials, natural materials, fabric, metals, wood, glass, Perspex, or a combination thereof. In some embodiments, substrate material is a non-conductive material, such as but not limited to polyester. Optionally, substrate base layer 58 can be any suitable size, shape or color.

Optionally, substrate base layer 58 may readily facilitate attachment of the patch 50 to a desired body area. Attachment mechanisms may include but are not limited to conductive adhesive, adhesive strip, suction cups and/or any combinations thereof. In the embodiment of FIG. 3A or 3B, patch 50 is configured to attach to the body area by conductive layers 60, 62. In alternate embodiments, the patch may be attached to the body area by, for example, the frame of the substrate and/or other attachment mechanisms.

Conductive layers 60 and 62 may optionally be any suitable conductive composition, such as an aqueous gel, hydrogel or a conductive adhesive.

The voltage provided by a patch of the present invention as described, for example, in FIG. 3A or 3B is dependent on the properties of the counter electrode 54 and active electrode 52 materials and the type of battery 56 used. In one non-limiting example wherein a zinc electrode of the present invention is connected to a silver/silver chloride counter electrode and wherein electrodes are connected to a power source 56, the resulting voltage is about 2 volts and the current is about 200 microamperes.

Electrode 52 employed in an electrotransport devices as described, for example, in FIG. 3A or 3B can be configured as a means for facilitating production of electrochemically generated metal ions. In an embodiment wherein electrode 52 is a zinc electrode as described hereinabove, electrode facilitates production of electrochemically generated zinc ions. The electrochemically generated metal ions are produced by the electrochemical reaction on the electrode, caused by the electric current flowing through electrode 52, which releases the insoluble electroactive metal ions. In some embodiments electrochemically generated metal ions, such as but not limited to zinc ions or copper ions or silver ions have medicinal, pharmaceutical, cosmeceutical or cosmetic properties and can be used for treatment and/or prevention of a disorder, such as an infection, viral infection, fungal infection, disease, allergy, parasite or other medical condition.

The electrodes of the present invention as described in FIGS. 2 and 3 hereinabove can be used in any type of active or passive electrotransport device or electrostimulation device. In some embodiments the electrodes of the present invention can be used in an electrotransport device which is galvanically powered or battery powered or solar powered or powered in any suitable way.

Figure 4:
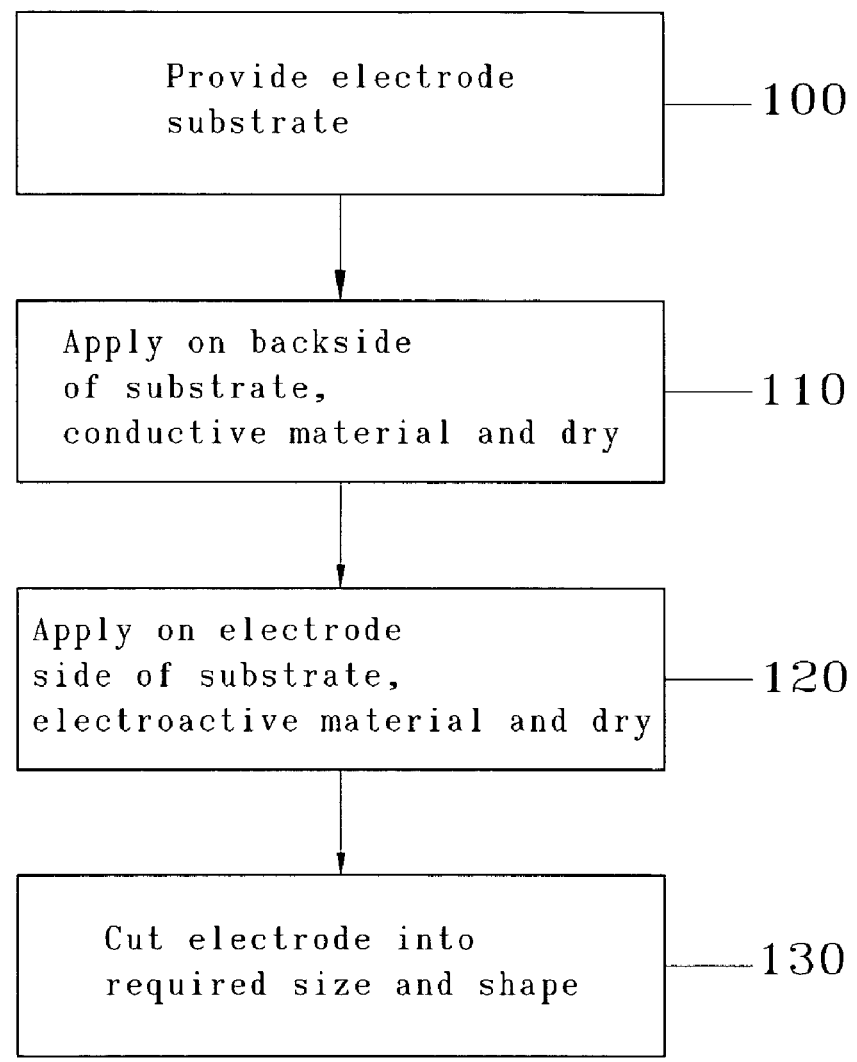
FIG. 4 shows a flowchart of a method of making an electrode according to one embodiment of the invention.

FIG. 4 shows a flowchart of an exemplary method of making an electrode according to one embodiment of the present invention. The flowchart applies to an electrode with a conductive substrate. A conductive substrate is provided 100. In some embodiments, the substrate is a vinyl web substrate. A conductive material is applied onto a backside of the conductive substrate and dried 110. Any suitable conductive material can be applied including a metallic or non-metallic conductive material. In some embodiments, the conductive material is silver and can be coated in a very thin layer of a few microns. In some embodiments, the conductive material is applied using any suitable printing technique. An electroactive material is applied to the electrode side of the conductive substrate and dried 120. In some embodiments, the electroactive substance is zinc. In some embodiments, the electroactive substance is applied using a printing technique. The electrode can be cut into any desired size and shape 130. The electrode can be attached to a battery in a further optional step 140. Alternatively, the electrode can be printed onto the same substrate as a printed battery, in a suitable way, such that the electrode is connected to the battery. The order of steps is not meant to be limiting and can be in any suitable order. The electrode of the present invention can be made in any suitable way. In some embodiments, the form of materials and technique of production used to make the electrode is dependent on factors such as the end use of the electrode and economical considerations. In some embodiments, it may be advantageous to apply the electrode materials as foil layers.

While the principles of the invention have been discussed in relation to exemplary embodiments discussed herein, it is understood that the principles of the invention are not limited thereto.

EXAMPLE 1

A Method of Making a Higher Powered Electrode with Uniform Current Distribution and High Capacity One side of a vinyl web was coated with silver using a printing technique, using draw down equipment. The silver ink applied was Acheson silver ink, but any silver ink can be used. The silver ink was then dried using a suitable drying technique. The dry thickness of the silver layer was preferably a few microns, from about 2 to about 5 microns. After drying of the silver layer, the second surface of the vinyl web substrate was coated with zinc ink. The zinc ink was composed of a high purity zinc powder, of about greater than 95% purity, a suitable resin/solvent system and graphite conductive particles. The vinyl web was coated with the zinc ink using a draw down applicator. The zinc layer was then dried using a suitable drying technique. After drying, the thickness of the zinc layer was about 25 microns. The capacity of the electrode can be controlled by the loading weight (thickness) of coating. The resulting electrode structure was a vinyl web with one side (backside) coated with a thin silver layer and a second side (electrode side) coated with zinc particles. The electrode was cut into the desired size and shape. Contact between battery and electrode was accomplished by means of an electrical conductive pressure sensitive adhesive film. Adhesion was preferably done from the backside of the electrode namely silver side.

EXAMPLE 2

In one non-limiting example of the electrode of the present invention, the electrode was used as part of a dermal patch. The anode of the patch included a vinyl film coated on one side with relatively pure zinc, resulting in a capacity of about 18 mA minute/cm2. The backside of the vinyl film was coated with a layer of silver to improve conductivity and ensure homogeneous current distribution along the electrode, which in one non-limiting example was linear shaped. The cathode included a vinyl film coated with silver/silver chloride, resulting in a capacity of 18 mA minute/cm2.

EXAMPLE 3

Vinyl substrate was coated with a 20µ layer of 40% (% W) zinc ink. The sheet resistance was 10.7Ω/square. The resistance of a strip 0.5 mm wide and 100 mm long was 270Ω. For comparison a vinyl substrate was coated with a 20µ layer of 40% zinc ink (% W) and coated from the backside with a 5µ layer of silver ink. The sheet resistance was 0.5Ω/square. The resistance of a strip 0.5 mm wide and 100 mm long was 1.2Ω. Therefore, it could be seen that the coating of a conductor, such as silver on the backside of the vinyl substrate resulted in a significantly lower sheet resistance, which is indicative of more uniform current distribution.

Those skilled in the art can appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

What is claimed is:

1. An electrode comprising:
(a) an electrode substrate, wherein the electrode substrate has an electrode side and a backside and wherein the electrode substrate comprises
  (I) a conductive substrate; or
  (II) a non-conductive substrate comprising at least one conductive via which extends from the backside to the electrode side of the electrode substrate;
(b) a conductive material layer which facilitates uniform current distribution and is disposed on the backside of the substrate; and
(c) at least one insoluble electroactive pole material disposed on the electrode side of the substrate;
wherein the conductive material layer is less reactive than the insoluble electroactive pole material.

2. The electrode of claim 1, wherein the conductive substrate is vinyl web.

3. The electrode of claim 1, wherein the conductive material layer is selected from the group consisting of silver, silver/silver chloride, gold, platinum, carbon and a combination thereof.

4. The electrode of claim 1, wherein the electroactive material is selected from the group consisting of zinc, copper, magnesium, silver, silver/silver chloride and iron and a combination thereof.

5. The electrode of claim 1 for providing a use selected from the group consisting of facilitating uniform current distribution, facilitating high capacity, facilitating higher power, higher current, cathode and/or anode in electrotransport device, cathode and/or anode in an electrostimulation device, facilitating improved delivery of active agent, facilitating improved penetration of membrane, facilitating electrochemically generating metal ions, use in a battery and a combination thereof.

6. A method of making an electrode comprising the steps of:
(a) providing an electrode substrate with a backside and an electrode side, wherein the electrode substrate comprises
  (i) a conductive substrate; or
  (ii) a non-conductive substrate comprising at least one conductive via which extends from the backside to the electrode side of the electrode substrate;
(b) applying a layer of conductive material to the back side of the substrate;
(c) drying the layer of conductive material;
(d) applying a layer of insoluble electroactive pole material to the electrode side of the substrate; and
(e) drying the layer of electroactive material.

7. The method of claim 6, wherein the insoluble electroactive material includes zinc.

8. The method of claim 6, wherein (b) and (d) are done using a printing technique.

9. A dermal patch comprising:
(a) at least one active electrode to make electrical contact with a first region of a body area, wherein the active electrode comprises:
  (i) an electrode substrate, wherein the electrode substrate has an electrode side and a backside and wherein the electrode substrate comprises
    (I) a conductive substrate; or
    (II) a non-conductive substrate comprising at least one conductive via which extends from the backside to the electrode side of the electrode substrate;
  (ii) a conductive material layer which facilitates uniform current distribution and is disposed on the backside of the substrate; and
  (iii) at least one insoluble electroactive pole material disposed on the electrode side of the substrate;
  wherein the conductive material layer is less reactive than the insoluble electroactive pole material;
(b) at least one counter electrode to make electrical contact with a second region of the body area; and
(c) at least one power source for supplying electrical energy to the active electrode and the counter electrode, wherein the power source is supported on a base member.

10. The patch of claim 9 for providing a use selected from the group consisting of facilitating uniform current distribution, facilitating high capacity, facilitating higher power, higher current, facilitating improved delivery of active agent, facilitating improved penetration of membrane, facilitating electrochemically generating metal ions from the active electrode and a combination thereof.

11. The dermal patch of claim 9, wherein conductive adhesive facilitates attachment of the at least one active electrode and the at least one counter electrode to the power source.

12. A dermal patch comprising:
(a) at least one active zinc electrode to make electrical contact with a first region of a body area, wherein the active electrode comprises:
  (i) an electrode substrate, wherein the electrode substrate has an electrode side and a backside and wherein the electrode substrate comprises
    (I) a conductive substrate; or
    (II) a non-conductive substrate comprising at least one conductive via which extends from the backside to the electrode side of the electrode substrate;
  (ii) a conductive material layer which facilitates uniform current distribution and is disposed on the backside of the substrate; and
  (iii) an insoluble electroactive pole material comprising zinc disposed on the electrode side of the substrate; wherein the conductive material layer is less reactive than the insoluble electroactive pole materiaL;
(b) at least one counter electrode to make electrical contact with a second region of the body area; and
(c) at least one power source for supplying electrical energy to the active electrode and the counter electrode, wherein the power source is supported on a base member.

13. The patch of claim 12 for providing a use selected from the group consisting of facilitating uniform current distribution, facilitating high capacity, facilitating higher power, higher current, facilitating improved delivery of an active agent, facilitating improved penetration of membrane, facilitating electrochemically generating zinc ions from the zinc electrode and a combination thereof.

14. The patch of claim 12 for electrochemically generating zinc ions from the zinc electrode, wherein the generated zinc ions are for treating and/or preventing a disorder.

* * * * *